(12) United States Patent
Niewöhner et al.

(10) Patent No.: US 6,683,081 B2
(45) Date of Patent: Jan. 27, 2004

(54) TRIAZOLOTRIAZINONES AND THE USE THEREOF

(75) Inventors: Ulrich Niewöhner, Wermelskirchen (DE); Helmut Haning, Milford, CT (US); Thomas Lampe, Wuppertal (DE); Mazen Es-Sayed, Langenfeld (DE); Gunter Schmidt, Wuppertal (DE); Erwin Bischoff, Wuppertal (DE); Klaus Dembowsky, Boston, MA (US); Elisabeth Perzborn, Wuppertal (DE); Karl-Heinz Schlemmer, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/149,921

(22) PCT Filed: Dec. 12, 2000

(86) PCT No.: PCT/EP00/12592

§ 371 (c)(1), (2), (4) Date: Oct. 21, 2002

(87) PCT Pub. No.: WO01/47929

PCT Pub. Date: Jul. 3, 2001

(65) Prior Publication Data

US 2003/0212064 A1 Nov. 13, 2003

(30) Foreign Application Priority Data

Dec. 24, 1999 (DE) .......................... 199 62 927
Jan. 27, 2000 (DE) .......................... 100 03 296

(51) Int. Cl.$^7$ .................. C07D 487/04; A61K 31/53
(52) U.S. Cl. .................. 514/243; 514/233.2; 514/218; 514/212.08; 540/599; 540/575; 544/184; 544/58.6; 544/112
(58) Field of Search .................. 544/184, 58.6, 544/112; 540/599, 575; 514/243, 212.08

(56) References Cited

U.S. PATENT DOCUMENTS 5,346,901 A    9/1994   Bell et al. .................. 514/258

FOREIGN PATENT DOCUMENTS

| AU | 738675 | 5/1999 |
| DE | 19812462 | 9/1999 |
| EP | 0463756 | 4/1995 |
| WO | 9306104 | 4/1993 |
| WO | 9400453 | 1/1994 |
| WO | 9719947 | 5/1997 |
| WO | 9849166 | 11/1998 |
| WO | 9924433 | 5/1999 |

OTHER PUBLICATIONS

Bhattacharya, B., Rao, T., Lewis, A., Revankar, G., "Synthesis of Certain N– and C–Alkyl Purine Analogs", J. Heterocyclic Chem., 30: 1341–1349 (1993).

Mitchell, W. Hill, M., Newton, R., Ravenscroft, P., Scopes, D., Synthesis of C–Nucleoside Isosteres of 9–(2–Hydroxyethoxymethyl) Guanine (Acyclovir), J. Heterocyclic Chem., 21: 697–699 (1984).

Rao, T., Revankar, G., "Synthesis of Certain Acyclic Nucleoside Analogs of 1,2,4–Triazolo[3,4–f][1,2,4] Triazine and Pryimido[5,4–d]Pyrimidine", Nucleosides & Nucleotides, 14(7): 1601–1612 (1995).

Ramasamy, K., Ugarkar, B., McKernan, P., Robins, R., Revankar, G., "Synthesis and Antitumor Activity of Certain 3–β–D–Ribofuranosyl–1,2,4–Triazolo[3,4–f]–1,2,4–Triazines Related to Formycin Prepared Via Ring Closure of a 1,2,4–Triazine Precursor", J. Med. Chem., 29: 2231–2235 (1986).

Beavo, J., Reifsnyder, D., "Primary Sequence of Cyclic Nucleotide Phosphodiesterase Isozymes and the Design of Selective Inhibitors", TIPS Reviews, 11: 150–155 (Apr., 1990).

Stoclet, J., Keravis, T., Komas, N., Lugnier, C., "Cyclic Nucleotide Phosphodiesterases as Therapeutic Targets in Cardiovascular Diseases", Exp. Opin. Invest. Drugs, 4(11): 1081–1100 (1995).

Primary Examiner—John M. Ford
(74) Attorney, Agent, or Firm—Susan M. Pellegrino

(57) ABSTRACT

The invention relates to novel triazolotriazinones of the general formula (I), to a method for their production and to the pharmaceutical use thereof.

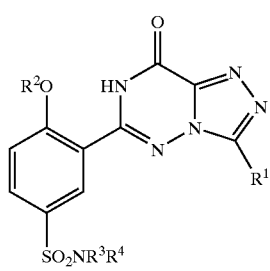

7 Claims, No Drawings

TRIAZOLOTRIAZINONES AND THE USE THEREOF

This is a 371 of PCT/EP00/12592, filed Dec. 12, 2000.

The present relates to novel triazolotriazinones, to processes for preparing them and to their use as medicaments, in particular as inhibitors of cGMP-metabolizing phosphodiesterases.

J. Heterocycl. Chem. (1993), 30(5), 1341–9, J. Heterocycl. Chem. (1984), 21(3), 697–9 and Nucleosides Nucleotides (1995), 14(7), 1601–12 describe 6-amino-triazolotriazinones which have an antiviral effect.

J. Med. Chem. (1986), 29(11), 2231–5 also describes 6-amino-triazolotriazinones as nucleoside analogs having an antitumor effect. Triazolotriazinones having the substituents described in the present invention and having an inhibitory effect against cGMP-metabolizing phosphodiesterases have not been disclosed.

The compounds according to the invention are potent inhibitors of cyclic guanosine 3',5'-monophophate-metabolizing phosphodiesterases (cGMP -PDEs). In accordance with the nomenclature of Beavo and Reifsnyder (Trends in Pharmacol. Sci. 11, 150–155, 1990), these phosphodiesterases are the phosphodiesterase isoenzymes PDE-I, PDE-II and PDE-V.

An increase in the concentration of cGMP can lead to therapeutic, antiaggregatory, antithrombotic, antiproliferative, antivasospastic, vasodilatory, natriuretic and diuretic effects. It can exert an effect on the short-term or long-term modulation of vascular and cardiac inotropy, cardiac rhythm and stimulus conduction in the heart (J. C. Stoclet, T. Keravis, N. Komas and C. Kugnier, Exp. Opin. Invest. Drugs (1995), 4 (11), 1081–1100). Inhibition of the cGMP-PDEs can also strengthen erection. These compounds are therefore suitable for treating erectile dysfunctions.

The present invention now relates to triazolotriazinones of the general formula (I),

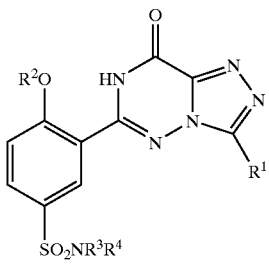

in which $R^1$ represents straight-chain or branched alkyl having up to 6 carbon atoms or represents $(C_3–C_8)$-cycloalkyl, $R^2$ represents hydrogen or represents straight-chain or branched alkyl having up to 6 carbon atoms, $R^3$ and $R^4$ are identical or different and represent hydrogen or $(C_1–C_6)$-alkoxy or represent $(C_1–C_6)$-alkyl which is optionally substituted, up to 3 times, identically or differently, by hydroxyl, $(C_1–C_5)$-alkoxy or phenoxy or by radicals of the formulae —O—CO—$NR^5R^6$, —$NR^7R^8$ or

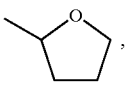

in which $R^5$, $R^6$, $R^7$ and $R^8$ are identical or different and denote hydrogen, $(C_1–C_6)$-alkyl or phenyl, or $R^7$ and $R^8$, together with the nitrogen atom to which they are bonded, form a 5- to 6-membered, saturated heterocycle which can additionally contain a further heteroatom from the series S and O, and/or $(C_1–C_6)$-alkyl is, for its part, optionally substituted by phenyl which is optionally substituted, up to 3 times, identically or differently, by hydroxyl, $(C_1–C_6)$-alkoxy or halogen or by $(C_1–C_6)$-alkyl which, for its part, is in turn substituted by hydroxyl or $(C_1–C_6)$-alkoxy, or phenyl is optionally substituted by radicals of the formulae —$SO_2$—$NR^9R^{10}$ or —$NR^{11}R^{12}$, in which $R^9$, $R^{10}$, $R^{11}$ and $R^{12}$ are identical or different and denote hydrogen, $(C_1–C_6)$-alkyl or phenyl, or $R^{11}$ and $R^{12}$, together with the nitrogen atom to which they are bonded, form a 5- to 6-membered, saturated heterocycle which can additionally contain a further heteroatom from the series S and O, or $R^3$ represents hydrogen or $(C_1–C_6)$-alkyl, and $R^4$ represents radicals of the formula

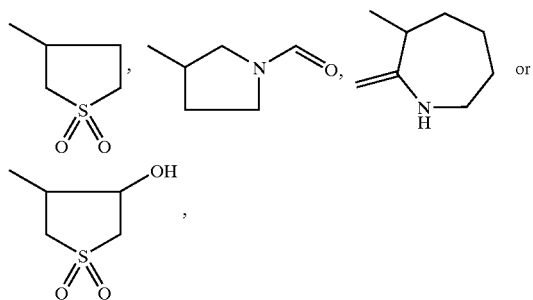

or represents phenyl which is optionally substituted, up to 3 times, identically or differently, by halogen, $(C_1–C_6)$-alkoxy or hydroxyl or by a radical of the formula

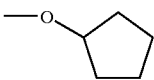

or by $(C_1–C_6)$-alkyl which, for its part, can be substituted by hydroxyl or $(C_1–C_6)$-alkoxy, or $R^3$ and $R^4$, together with the nitrogen atom to which they are bonded, form a radical of the formula

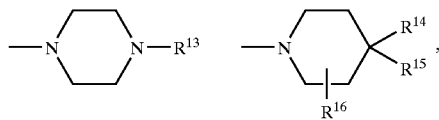

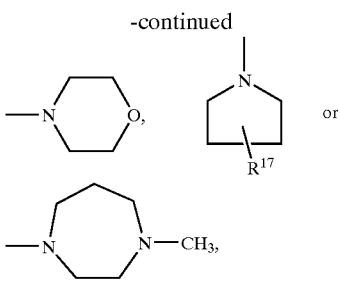

in which
R$^{13}$ denotes hydrogen, (C$_1$–C$_6$)-alkoxycarbonyl, (C$_3$–C$_6$)-cycloalkyl, pyridyl, pyrimidyl or (C$_1$–C$_6$)-alkyl which is optionally substituted by hydroxyl, R$^{14}$ and R$^{15}$ are identical or different and denote hydrogen, hydroxyl or (C$_1$–C$_6$)-alkyl which is optionally substituted by hydroxyl or by a radical of the formula —P(O)(OR$^{18}$)(OR$^{19}$), in which
R$^{18}$ and R$^{19}$ are identical or different and denote hydrogen or (C$_1$–C$_6$)-alkyl, or R$^{14}$ and R$^{15}$ together form a radical of the formula =N—OH, R$^{16}$ and R$^{17}$ are identical or different and denote hydrogen or (C$_1$–C$_6$)-alkyl which is optionally substituted by hydroxyl, and the salts, N-oxides and isomeric forms thereof.

The compounds according to the invention can exist in stereoisomeric forms which either relate to each other as image and mirror image (enantiomers) or which do not relate to each other as image and mirror image (diastereomers). The invention relates to both the enantiomers or diastereomers or their respective mixtures. The racemic forms, as well as the diastereomers, can be separated into the stereoisomerically uniform constituents in a known manner.

The substances according to the invention can also be present as salts. Within the context of the invention, preference is given to physiologically harmless salts.

Physiologically harmless salts can be salts of the compounds according to the invention with inorganic or organic acids. Preference is given to salts with inorganic acids, such as hydrochloric acid, hydrobromic acid, phosphoric acid or sulfuric acid, or salts with organic carboxylic or sulfonic acid, such as acetic acid, maleic acid, fumaric acid, malic acid, citric acid, tartaric acid, lactic acid or benzoic acid, or methanesulfonic acid, ethanesulfonic acid, phenylsulfonic acid, toluenesulfonic acid or naphthalenedisulfonic acid.

Physiologically harmless salts can equally well be metal or ammonium salts of the compounds according to the invention. Particular preference is given, for example, to sodium, potassium, magnesium or calcium salts, and also to ammonium salts which are derived from ammonia, or to organic amines, such as ethylamine, di- or triethylamine, di- or triethanolamine, dicyclohexylamine, dimethylaminoethanol, arginine, lysine, ethylenediamine or 2-phenylethylamine.

(C$_3$–C$_8$)-Cycloalkyl and/or (C$_3$–C$_6$)-cycloalkyl represents cyclopropyl, cyclopentyl, cyclobutyl, cyclohexyl, cycloheptyl or cyclooctyl. Those which may be mentioned as being preferred are: cyclopropyl, cyclopentyl and cyclohexyl.

(C$_1$–C$_6$)-Alkyl represents a straight-chain or branched alkyl radical having from 1 to 6 carbon atoms. Those which may be mentioned by way of example are: methyl, ethyl, n-propyl, isopropyl, n-butyl, isobutyl, tert-butyl, n-pentyl and n-hexyl. Preference is given to a straight-chain or branched alkyl radical having from 1 to 4 carbon atoms. Particular preference is given to a straight-chain or branched alkyl radical having from 1 to 3 carbon atoms.

(C$_1$–C$_6$)-Alkoxy represents a straight-chain or branched alkoxy radical having from 1 to 6 carbon atoms. Those which may be mentioned by way of example are: methoxy, ethoxy, n-propoxy, isopropoxy, n-butoxy, isobutoxy, tert-butoxy, n-pentoxy and n-hexoxy. Preference is given to a straight-chain or branched alkoxy radical having from 1 to 4 carbon atoms. Particular preference is given to a straight-chain or branched alkoxy radical having from 1 to 3 carbon atoms.

Within the context of the invention, (C$_1$–C$_6$)-alkoxycarbonyl represents a straight-chain or branched alkoxycarbonyl radical having from 1 to 6 carbon atoms. Those which may be mentioned by way of example are: methoxycarbonyl, ethoxycarbonyl, n-propoxycarbonyl, isopropoxycarbonyl and tert-butoxycarbonyl. Preference is given to a straight-chain or branched alkoxycarbonyl radical having from 1 to 4 carbon atoms. Particular preference is given to a straight-chain or branched alkoxycarbonyl radical having from 1 to 3 carbon atoms.

In general, halogen represents fluorine, chlorine, bromine and iodine. Preference is given to fluorine, chlorine and bromine. Particular preference is given to fluorine and chlorine.

A 5- to 6-membered aromatic heterocycle having up to 3 heteroatoms from the series S, O and/or N represents, for example, pyridyl, pyrimidyl, pyridazinyl, thienyl, furyl, pyrrolyl, thiazolyl, oxazolyl or imidazolyl. Preference is given to pyridyl, pyrimidyl, pyridazinyl, furyl and thienyl.

Preference is given to compounds according to the invention of the general formula (I), in which R$^1$ represents straight-chain or branched alkyl having up to 5 carbon atoms, or represents cyclopropyl, cyclopentyl or cyclohexyl, R$^2$ represents straight-chain or branched alkyl having up to 4 carbon atoms, R$^3$ and R$^4$ are identical or different and represent hydrogen or methoxy or represent (C$_1$–C$_5$)-alkyl which is optionally substituted, up to 3 times, identically or differently, by hydroxyl, (C$_1$–C$_4$)-alkoxy or phenoxy or by groups of the formulae —O—CO—NR$^5$R$^6$, —NR$^7$R$^8$ or

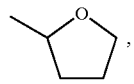

in which
R$^5$, R$^6$, R$^7$ and R$^8$ are identical or different and denote hydrogen, (C$_1$–C$_4$)-alkyl or phenyl, or R$^7$ and R$^8$, together with the nitrogen atom to which they are bonded, form a morpholine, piperidine or pyrrolidine ring, and/or (C$_1$–C$_5$)-alkyl is, for its part, optionally substituted by phenyl which can be optionally substituted, up to 3 times, identically or differently, by hydroxyl or (C$_1$–C$_4$)-alkoxy or by (C$_1$–C$_4$)-alkyl which, for its part, is in turn substituted by hydroxyl or (C$_1$–C$_4$)-alkoxy, or phenyl is optionally substituted by radicals of the formulae —SO$_2$—NR$^9$R$^{10}$ or —NR$^{11}$R$^{12}$, in which R$^9$, R$^{10}$, R$^{11}$ and R$^{12}$ are identical or different and denote hydrogen, (C$_1$–C$_4$)-alkyl or phenyl, or R$^{11}$ and R$^{12}$, together with the nitrogen atom to which they are bonded, form a morpholine, piperidine or pyrrolidine ring, or $R^3$ represents hydrogen or $(C_1-C_4)$-alkyl, and $R^4$ represents radicals of the formula

[structures: 3-methyl-tetrahydrothiophene-1,1-dioxide; 3-methyl-1-formyl-pyrrolidine; 3-methyl-caprolactam; 3-methyl-4-hydroxy-tetrahydrothiophene-1,1-dioxide]

or represents phenyl which is optionally substituted, up to 3 times, identically or differently, by fluorine, $(C_1-C_4)$-alkoxy or hydroxyl, by a radical of the formula

[structure: —O—cyclopentyl]

or by $(C_1-C_4)$-alkyl which can, for its part, be substituted by hydroxyl or $(C_1-C_3)$-alkoxy, or $R^3$ and $R^4$, together with the nitrogen atom to which they are bonded, form a radical of the formula

[structures: piperazinyl-$R^{13}$; piperidinyl with $R^{14}$, $R^{15}$, $R^{16}$; morpholino; pyrrolidinyl-$R^{17}$; 4-methyl-homopiperazinyl]

in which $R^{13}$ denotes hydrogen, $(C_1-C_4)$-alkoxycarbonyl, cyclopentyl, cyclohexyl, pyridyl, pyrimidyl or $(C_1-C_5)$-alkyl which is optionally substituted by hydroxyl, $R^{14}$ and $R^{15}$ are identical or different and denote hydrogen or $(C_1-C_5)$-alkyl which is optionally substituted by hydroxyl or by a radical of the formula —P(O)(OR$^{18}$)(OR$^{19}$), in which $R^{18}$ and $R^{19}$ are identical or different and denote hydrogen, methyl or ethyl, or $R^{14}$ and $R^{15}$ together form a radical of the formula =N—OH, $R^{16}$ and $R^{17}$ are identical or different and denote hydrogen, hydroxyl or $(C_1-C_3)$-alkyl which is optionally substituted by hydroxyl, and the salts, N-oxides and isomeric forms thereof.

Particular preference is given to compounds of the general formula (I), in which $R^1$ represents straight-chain or branched alkyl having up to 3 carbon atoms or represents cyclopentyl, $R^2$ represents straight-chain or branched alkyl having up to 3 carbon atoms, $R^3$ and $R^4$ are identical or different and represent hydrogen or methoxy or represent $(C_1-C_4)$-alkyl which is optionally substituted, up to 3 times, identically or differently, by hydroxyl, $(C_1-C_4)$-alkoxy or phenoxy or by groups of the formulae —O—CO—NR$^5$R$^6$, —NR$^7$R$^8$ or

[structure: 2-methyl-tetrahydrofuran]

in which $R^5$, $R^6$, $R^7$ and $R^8$ are identical or different and denote hydrogen, $(C_1-C_3)$-alkyl or phenyl, or $R^7$ and $R^8$, together with the nitrogen atom to which they are bonded, form a morpholine, piperidine or pyrrolidine ring, and/or $(C_1-C_4)$-alkyl is, for its part, optionally substituted by phenyl which is optionally substituted, up to 3 times, identically or differently, by hydroxyl, $(C_1-C_3)$-alkoxy or fluorine or by $(C_1-C_3)$-alkyl which is for its part in turn substituted by hydroxyl or $(C_1-C_4)$-alkoxy, or phenyl is optionally substituted by radicals of the formulae —SO$_2$—NR$^9$R$^{10}$ or —NR$^{11}$R$^{12}$, in which $R^9$, $R^{10}$, $R^{11}$ and $R^{12}$ are identical or different and denote hydrogen, $(C_1-C_3)$-alkyl or phenyl, or $R^{11}$ and $R^{12}$, together with the nitrogen atom to which they are bonded, form a morpholine, piperidine or pyrrolidine ring, or $R^3$ represents hydrogen or methyl, and $R^4$ represents radicals of the formula

[structures: 3-methyl-tetrahydrothiophene-1,1-dioxide; 3-methyl-1-formyl-pyrrolidine; 3-methyl-caprolactam; 3-methyl-4-hydroxy-tetrahydrothiophene-1,1-dioxide]

or represents phenyl which is optionally substituted, up to 3 times, identically or differently, by fluorine, methoxy or hydroxyl, by a radical of the formula

[structure: —O—cyclopentyl]

or by $(C_1-C_4)$-alkyl which, for its part, can be substituted by hydroxyl or methoxy or ethoxy, or $R^3$ and $R^4$, together with the nitrogen atom to which they are bonded, form a radical of the formula

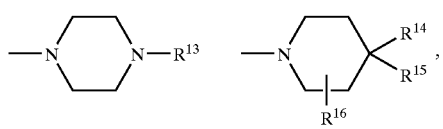 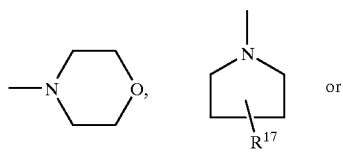

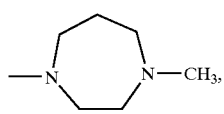 or

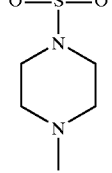

in which

R$^{13}$ denotes hydrogen, (C$_1$–C$_4$)-alkoxycarbonyl, cyclopentyl, pyrimidyl or (C$_1$–C$_3$)-alkyl which is optionally substituted by hydroxyl, R$^{14}$ and R$^{15}$ are identical or different and denote (C$_1$–C$_3$)-alkyl which is optionally substituted by hydroxyl or by a radical of the formula —P(O)(OR$^{18}$)(OR$^{19}$), in which R$^{18}$ and R$^{19}$ denote ethyl, or R$^{14}$ and R$^{15}$ together form a radical of the formula =N—OH, R$^{16}$ and R$^{17}$ are identical or different and denote hydrogen or (C$_1$–C$_3$)-alkyl which is optionally substituted by hydroxyl, and the salts, N-oxides and isomeric forms thereof.

Very particular preference is given to the compounds which are listed in the following table:

Structure

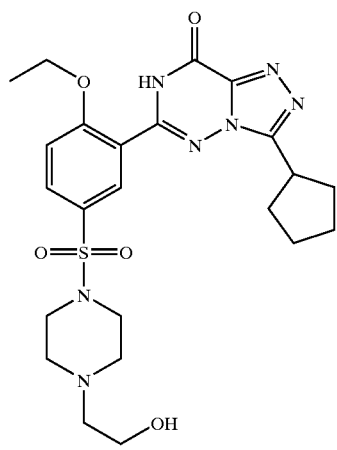

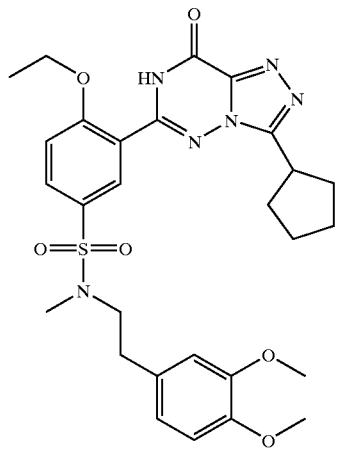

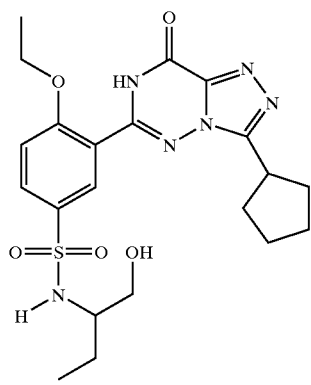

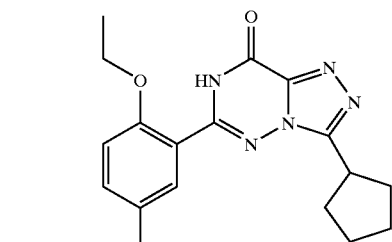

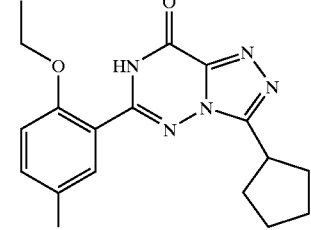

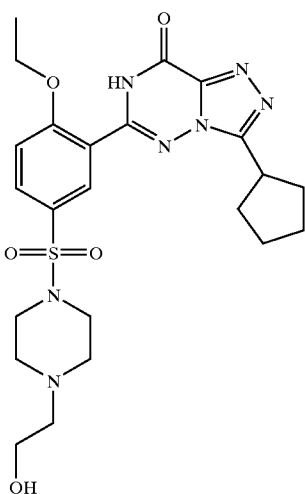

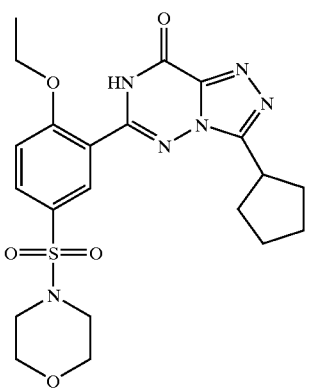

In addition, a process was found for preparing the compounds according to the invention of the general formula (I), which process is characterized in that compounds of the general formula (II)

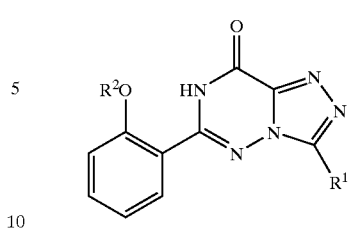

in which

R¹ and R² have the abovementioned meaning, is reacted with chlorosulfonic acid (ClSO₃H), where appropriate in inert solvents and where appropriate in the presence of a base, to give the compounds of the general formula (III)

in which

R¹ and R² have the abovementioned meaning, and subsequently reacted with amines of the general formula (IV)

HNR³R⁴      (IV), in which

R³ and R⁴ have the abovementioned meaning.

The process according to the invention can be explained, by way of example, by the following formula scheme:

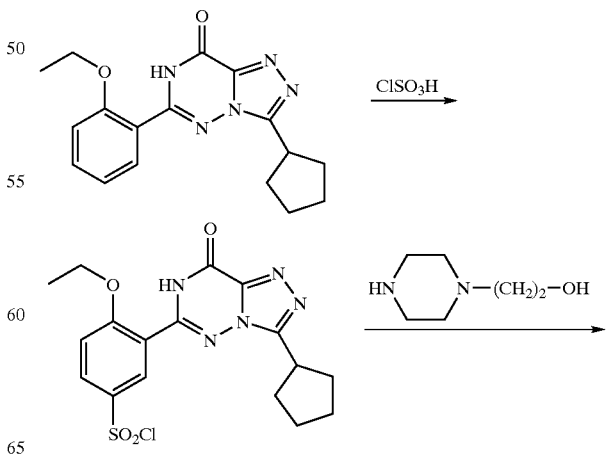

-continued

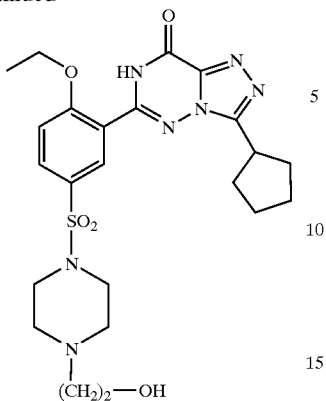

Solvents which are suitable for the individual steps are the customary organic solvents which are not altered under the reaction conditions. These solvents preferably include ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethane, trichloroethylene or chlorobenzene, or ethyl acetate, dimethylformamide, hexamethylphosphoric triamide, acetonitrile, acetone, dimethoxyethane or pyridine. It is likewise possible to use mixtures of the abovementioned solvents.

In general, the reaction temperatures can vary over a relatively wide range. In general, the temperatures employed are in a range of from −20° C. to 200° C., preferably of from 0° C. to 70° C.

In general, the process steps according to the invention are carried out under standard pressure. However, it is also possible to carry them out under positive pressure or under negative pressure (e.g. in a range from 0.5 to 5 bar).

The reactions can, for example, take place in a temperature range of from 0° C. to room temperature and under standard pressure.

The compounds of the general formula (II) are novel and can be prepared by preparing, by means of reacting the compounds of the general formula (V)

 (V), in which

R$^1$ has the abovementioned meaning, with thiocarbohydrazide

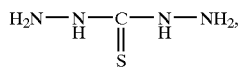

the compounds of the general formula (VI)

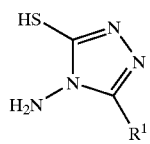 (VI), in which

R$^1$ has the abovementioned meaning, then converting these compounds, by reaction with H$_2$O$_2$/CH$_3$CO$_2$H, into the compounds of the general formula (VII)

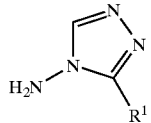 (VII), in which

R$^1$ has the abovementioned meaning, and, in a further step, by means of reacting these compounds with compounds of the general formula (VIII)

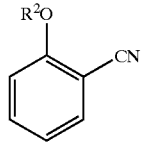 (VIII), in which

R$^2$ has the abovementioned meaning, preparing the compounds of the general formula (IX)

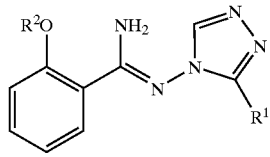 (IX), in which

R$^1$ and R$^2$ have the abovementioned meaning, and subsequently converting these compounds, with diethyl carbonate, into compounds of the general formula (X)

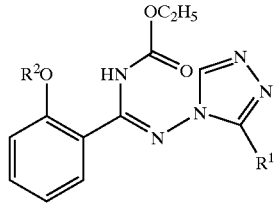 (X), in which

R$^1$ and R$^2$ have the abovementioned meaning, and finally cyclizing these compounds by heating to give the compounds of the general formula (II).

Solvents which are suitable for the individual steps are the customary organic solvents which are not altered under the reaction conditions. These solvents preferably include ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethane, trichloroethylene or chlorobenzene, or ethyl acetate, dimethylformamide, hexamethylphosphoric triamide, acetonitrile, acetone, dimethoxyethane or pyridine. It is likewise possible to use mixtures of the abovementioned solvents.

In general, the reaction temperatures can vary within a relatively wide range. In general, the temperatures employed are in a range from −20° C. to 200° C., preferably of from 0° C. to 70° C.

The process steps according to the invention are generally carried out under standard pressure. However it is also possible to carry them out under positive pressure or under negative pressure (e.g. in a range from 0.5 to 5 bar).

The reactions can, for example, take place in a temperature range of from 0° C. to room temperature and under standard pressure.

The compounds of the general formulae (III), (IX) and (X) are novel and can be prepared, for example, as described above.

The compounds of the general formulae (IV), (V), (VI), (VII) and (VIII) are known and can be prepared using customary methods.

The compounds according to the invention of the general formula (I) exhibit a valuable pharmacological spectrum of activity which it was not possible to foresee.

They inhibit either one or several of the c-GMP-metabolizing phosphodiesterases (PDE I, PDE II and PDE V). This leads to an increase in c-GMP. The differing expression of the phosphodiesterases in different cells, tissues and organs, as well as the differing subcellular location of these enzymes, make it possible, in combination with the selective inhibitors according to the invention, to address the different cGMP-regulated processes selectively.

In addition, the compounds according to the invention augment the effect of substances such as EDRF (endothelium-derived relaxing factor) and ANP (atrial natriuretic peptide), of nitro vasodilators and all other substances which increase the concentration of the cGMP in another way than phosphodiesterase inhibitors.

The compounds according to the invention of the general formula (I) are therefore suitable for the prophylaxis and/or treatment of diseases in which an increase in the concentration of cGNT is therapeutic, i.e. diseases which are connected with cGNT-regulated processes (in English, usually simply termed cGMP-related diseases). These diseases include cardiovascular diseases, diseases of the urogenital system and cerebrovascular diseases.

Within the meaning of the present invintn, the term "cardiovascular diseases" covers diseases such as high blood pressure, neuronal hypertension, stable and unstable angina, peripheral and cardiac vascular diseases, arrhythmias, thromboembolic diseases and ischemias such as myocardial infarction, stroke, transistory and ischemic attacks, angina pectoris and peripheral circulatory disturbances, and also prevention of restenoses following thrombolysis therapy, percutaneous transluminal angioplasty (PTA), percutaneous transluminal coronary angioplasties (PTCA) and bypass.

Furthermore, the compounds according to the invention of the general formula (I) can also have importance for cerebrovascular diseases. These include, for example, cerebral ischemia, stroke, reperfusion damage, brain trauma, edemas, cerebral thromboses, dementia and Alzheimer's disease.

The relaxing effect on smooth musculature makes them suitable for treating disorders of the urogenital system such as prostate hypertrophy and incontinence and also, in particular, for treating erectile dysfunction and female sexual dysfunction.

Activity of the Phosphordiesterases (PDEs)

The cGMP-stimulatable PDE II, the cGMP-inhibitable PDE III and the cAMP-specific PDE IV were isolated either from porcine heart myocardium or from bovine heart myocardium. The $Ca^{2+}$-calmodulin-stimulatable PDE I was isolated from porcine aorta, porcine brain or, preferably, from bovine aorta. The c-GMP-specific PDE V was obtained from porcine small intestine, porcine aorta, human blood platelets and, preferably, from bovine aorta. Purification was effected by means of anion exchange chromatography on Pharmacia MonoQ$^R$, essentially in accordance with the method described by M. Hoey and Miles D. Houslay, Biochemical Pharmacology, Vol. 40, 193–202 (1990) and C. Lugman et al. Biochemical Pharmacology Vol. 35 1743–1751 (1986).

The enzyme activity is determined in a 100 $\mu$l test mixture, in 20 mM Tris/HCl buffer pH 7.5, which contains 5 mM $MgCl_2$, 0.1 mg of bovine serum albumin/ml and either 800 Bq of $^3$HcAMP or $^3$HcGMP. The final concentration of the corresponding nucleotides is $10^{-6}$ mol/l. The reaction is started by adding the enzyme, with the quantity of enzyme being measured such that approx. 50% of the substrate is transformed during the incubation time of 30 min. In order to test the cGMP-stimulatable PDE II, $^3$HcAMP is used as the substrate and $10^{-6}$ mol of unlabeled cGMP/l is added to the mixture. In order to test the $Ca^{2+}$-calmodulin-dependent PDE I, 1 $\mu$M $CaCl_2$ and 0,1 $\mu$M calmodulin are additionally added to the reaction mixture. The reaction is stopped by adding 100 $\mu$l of acetonitrile which contains 1 mM cAMP and 1 mM AMP. 100 $\mu$l of the reaction mixture are separated by HPLC and the cleavage products are determined quantitatively online using a flow-through scintillation counter. The substance concentration at which the reaction rate is decreased by 50% is measured. The "phosphodiesterase [$^3$H] cAMP-SPA enzyme assay" and the "phosphodiesterase [$^3$H] cGMP-SPA enzyme assay", supplied by Amersham Life Science, were additionally used for testing. The test was carried out using the experimental protocol specified by the manufacturer. The [$^3$H] cAMP-SPA assay was used for determining the activity of PDE II, with $10^{-6}$ M cGMP being added to the reaction mixture for the purpose of activating the enzyme. $10^{-7}$ M calmodulin and 1 $\mu$M $CaCl_2$ were added to the reaction mixture for the purpose of measuring PDE I. PDE V was measured using the [$^3$H] cGMP-SPA assay.

In principle, the inhibition of one or more phosphodiesterases of this type leads to an increase in the concentration of cGMP. As a result, the compounds are of interest for all therapies in which an increase in the concentration of cGMP can be assumed to be therapeutic.

The investigation of the cardiovascular effects was carried out on normotensive rats and on SH rats and on dogs. The substances were administered intravenously or orally.

The examination for erection-inducing effects was carried out on conscious rabbits [H. Nagamuma, T. Egashira, J. Fuji, Clinical and Experimental Pharmacology and Physiology 20, 177–183 (1993)]. The substances were administered orally or parenterally.

The novel active compounds, and also their physiologically harmless salts (e.g. hydrochlorides, maleates or lactates), can be converted, in a known manner, into the customary formulations, such as tablets, coated tablets, pills, granules, aerosols, syrups, emulsions, suspensions and solutions, using inert, nontoxic, pharmaceutically suitable carrier substances or solvents. In this connection, the therapeutically effective compound should in each case be present at a concentration of from about 0.5 to 90% by weight of the total mixture, i.e. in quantities which are sufficient for achieving the specified dosage range.

The formulations are prepared, for example, by extending the active compounds with solvents and/or carrier substances, where appropriate using emulsifiers and/or dispersants, with it being possible, for example when using water as a diluent, to use organic solvents as auxiliary solvents, where appropriate.

The administration is effected in a customary manner, preferably orally, transdermally or parenterally, for example perlingually, by the buccal route, intravenously, nasally, rectally or by inhalation.

For use in humans, doses of from 0.001 to 50 mg/kg, preferably 0.01 mg/kg–20 mg/kg, are generally administered when administering orally. A dose of 0.001 mg/kg–0.5 mg/kg is expedient when administering parenterally, for example by way of mucosae, nasally, by the buccal route or by inhalation.

Despite this, it can be necessary, where appropriate, to depart from the abovementioned quantities, specifically in dependence on the body weight or the nature of the route of administration, on the individual response to the medicament, on the nature of its formulation and on the time or interval at which the administration takes place. Thus, it can in some cases be sufficient to make do with less than the abovementioned smallest quantity whereas, in other cases, the abovementioned upper limit has to be exceeded. When relatively large quantities are being administered, it may be advisable to divide up these quantities into several individual doses which are given during the course of the day.

The compounds according to the invention are also suitable for use in veterinary medicine. For uses in veterinary medicine, the compounds, or their nontoxic salts, can be administered in a suitable formulation, in accordance with common veterinary procedures. The veterinarian can establish the nature of the application, and the dose, in accordance with the nature of the animal to be treated.

In the following examples of preparing the precursors and end products, it is always necessary, in structural formulae containing one or more unsaturated valences on the nitrogen atom or oxygen atom, to add a hydrogen.

In other words, in structures containing, for example, a structural element "—N—", what is meant is actually "—NH—", and in structures containing, for example, a structural element "—O", what is meant is actually "—OH".

PREPARING THE PRECURSORS

EXAMPLE I

4-Amino-5-cyclopentyl-4H-1,2,4-triazole-3-thiol

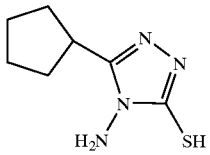

34.29 g (323 mmol) of finely mortared thiocarbohydrazide are suspended in 38.5 ml (355.3 mmol) of cyclopentanecarboxylic acid and the suspension is heated at 165° C. for 20 min. During this, the water produced in the reaction is distilled off until a yellowish condensate appears. After cooling down, 250 ml of dichloromethane/methanol 95:5 are added to the suspension and the precipitate is filtered off. The filtrate is concentrated and subject to column filtration on silica gel (dichloromethane/methanol 98:2). After drying under high vacuum, the product is obtained as a colorless solid.

Yield: 34.37 g, 75% purity (43.3% of theory)

MS (ESI-pos.): m/z (%)=185 (M+H) (53), 184 (M$^+$) (100), 143 (85)

$^1$H-NMR (200 MHz, CDCl$_3$): δ=1.58–2.17 (m, 8 H); 2.70–2.82 (m, 1 H); 3.20–3.35 (m, 1 H); 4.51 (s, 2 H).

EXAMPLE II

3-Cyclopentyl-4H-1,2,4-triazole-4-amine

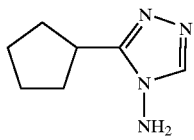

34.4 g (75% purity, 140 mmol) of the compound from example I are initially introduced in 250 ml of acetic acid, and 66 ml of 30% hydrogen peroxide solution are added in portions while refluxing. After the addition has finished, the mixture is stirred for 30 min at reflux and then concentrated after having been cooled down; the mixture is then made alkaline using 3 N sodium hydroxide solution. The aqueous phase is extracted six times with dichloromethane. After the organic phases have been combined, they are washed with a little saturated sodium chloride solution, dried over magnesium sulfate and concentrated. The slightly yellowish solid which accumulates is crystallized from dichloromethane/ether.

Yield: 3.99 g (15.4% of theory)

MS (DCI, NH$_3$): m/z (%)=153 (M+H) (100)

$^1$H-NMR (400 MHz, CDCl$_3$): δ=1.65–1.98 (m, 7 H); 2.03–2.12 (m, 2 H); 3.27 (qui, 1 H); 4.86 (s, 2 H); 8.10 (s, 1 H).

EXAMPLE III

N-(3-Cyclopentyl-4H-1,2,4-triazol-4-yl)-2-ethoxybenzenecarboximide-amide

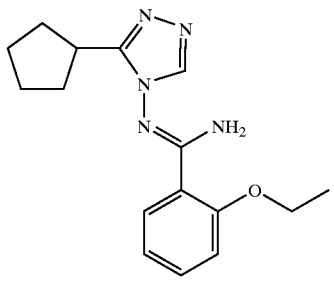

The compound from example II is added, as a solid (1.22 g, 8.02 mmol), to a suspension of 0.34 g (60%, 8.42 mmol) of NaH in 24 ml of dry 1,4-dioxane (baked-out flask, under argon). The suspension is stirred at 90° C. for 30 min before 1.30 g (8.82 mmol) of 2-ethoxybenzonitrile are added. The resulting suspension is stirred overnight at 90° C. After water has been added, the mixture is extracted (four times) with dichloromethane. The combined organic phases are washed with a little saturated sodium chloride solution and dried over magnesium sulfate. After concentrating down to approximately 20 ml, cyclohexane is added and the solid which is precipitated out is isolated by filtering it off.

Yield: 1.58 g (65.8% of theory)

MS (DCI, NH$_3$): m/z (%)=300 (M+H) (100)

$^1$H-NMR (200 MHz, CDCl$_3$): δ=1.51 (t, 3 H); 1.56–2.12 (m, 8 H); 3.14 (qui, 1 H);

4.22 (q, 2 H); 6.49 (bs, 2 H); 7.02–7.15 (m, 2 H); 7.49 (dt, 1 H); 8.04 (s, 1 H); 8.18 (dd, 1 H).

EXAMPLE IV

Ethyl [(3-cyclopentyl-4H-1,2,4-triazol-4-yl)-imido]-(2-ethoxyphenyl)methyl-carbamate

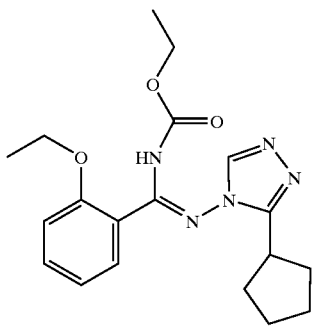

1.58 g (5.28 mmol) of the compound from example III are added as a solid, and 1.02 ml (8.4 mmol) of diethyl carbonate are added dropwise, to a suspension of 0.23 g (60%, 5.8 mmol) of sodium hydride in 26 ml of dry 1,4-dioxane (baked-out flask, argon). The suspension is stirred overnight at 90° C. After it has been cooled down, a further 120 mg of sodium hydride and 1.02 ml of diethyl carbonate are added and the mixture is stirred at 90° C. for a further 4 h before it is neutralized, after having been cooled, with 1 N hydrochloric acid solution and subsequently concentrated in vacuo. The residue is treated with a little water and extracted (four times) with dichloromethane. The combined organic phases are washed with a little saturated sodium chloride solution, dried over magnesium sulfate, concentrated and dried under high vacuum.

Yield: 2.14 g, 90% purity (98.2% of theory)

MS (DCI, NH$_3$): m/z (%)=372 (M+H) (100)

EXAMPLE V

3-Cyclopentyl-6-(2-ethoxyphenyl)[1,2,4]triazolo[3,4-f][1,2,4]triazin-8(7H)-one

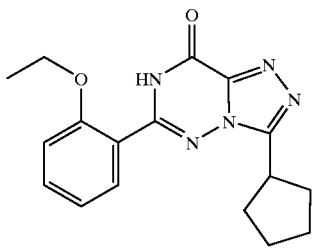

A solution consisting of 2.14 g (90%, 5.19 mmol) of the compound from example IV in 20 ml of 2-ethoxyethanol is heated overnight under reflux. After it has been cooled down, the mixture is subjected to rotary evaporation under high vacuum and dried on an oil pump. The solid residue is treated with hot ether and the solid which precipitates out is filtered off and dried under high vacuum.

Yield: 1.367 g (81% of theory)

MS (DCI, NH$_3$): m/z (%)=326 (M+H) (100)

$^1$H-NMR (200 MHz, CDCl$_3$): δ=1.62 (t, 3 H); 1.72–2.30 (m, 8 H); 3.68 (qui, 1 H);

4.34 (q, 2 H); 7.08–7.21 (m, 2 H); 7.04 (dt, 1 H); 8.25 (dd, 1 H); 10.85 (bs, 1 H).

EXAMPLE VI 3-(3-Cyclopentyl-8-oxo-7,8-dihydro[1,2,4]triazolo[3,4-f][1,2,4]triazin-6-yl)-4-ethoxybenzenesulfonyl chloride

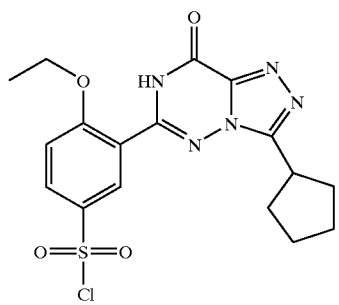

683 mg (2.1 mmol) of the compound from example V are introduced in portions into 1.68 ml (25.2 mmol) of ice-cooled chlorosulfonic acid. After having been warmed to room temperature, the mixture is then stirred overnight. After having been cooled down to 0° C., it is diluted with dichloromethane and the whole is poured onto ice water. The organic phase is separated off. The aqueous phase is extracted once again with dichloromethane, after which the organic phases are combined, washed with a little saturated sodium chloride solution, dried over magnesium sulfate and evaporated.

Yield: 801 mg (90% of theory)

MS (DCI, NH$_3$): m/z (%)=424 (M+H) (100)

$^1$H-NMR (200 MHz, CDCl$_3$): δ=1.65 (t, 3 H); 1.72–2.32 (m, 8 H); 3.71 (qui, 1 H);

4.47 (q, 2 H); 7.30 (d, 1 H); 8.22 (dd, 1 H); 8.77 (d, 1 H); 10.76 (bs, 1 H).

PREPARING THE ACTIVE COMPOUNDS

EXAMPLE 1

3-Cyclopentyl-6-(2-ethoxy-5-{[4-(2-hydroxyethyl)piperazino]sulfonyl}phenyl)-[1,2,4]triazolo[3,4-f][1,2,4]triazin-8-(7H)-one

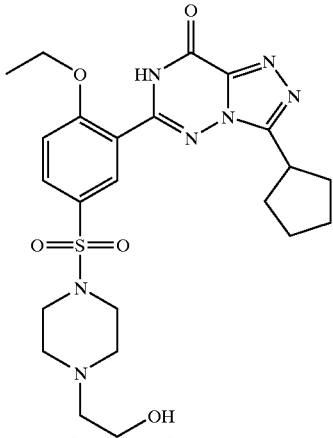

394 mg (2.8 mmol) of N-hydroxyethylpiperazine and a small spatula tip of 4-N-dimethylaminopyridine (DMAP) are added to a suspension consisting of 395 mg (0.92 mmol) of the sulfonyl chloride from example VI in 3 ml of dichloromethane; the resulting clear solution is stirred at room temperature before it is diluted, after 7 hours, with dichloromethane, washed with a little water and saturated sodium chloride, dried over magnesium chloride and concentrated in vacuo. The residue is crystallized from a little dichloromethane/ether.

Yield: 368 mg (72.5% of theory)

MS (DCI, $NH_3$): m/z (%)=518 (M+H) (100)

$^1$H-NMR (200 MHz, $CDCl_3$): δ=1.62 (t, 3 H); 1.68–2.30 (m, 8 H); 2.52–2.70 (m, 6 H); 3.05–3.17 (m, 4 H); 3.52–3.71 (m, 3 H); 4.49 (q, 2 H); 7.22 (d, 1 H); 7.91 (dd, 1 H); 8.43 (bs, 1 H); 10.64 (bs, 1 H).

EXAMPLE 2

3-(3-Cyclopentyl-8-oxo-7,8-dihydro[1,2,4]triazolo[3,4-f][1,2,4]triazin-6-yl)-N-(3,4-dimethoxyphenethyl)-4-ethoxy-N-methylbenzenesulfonamide

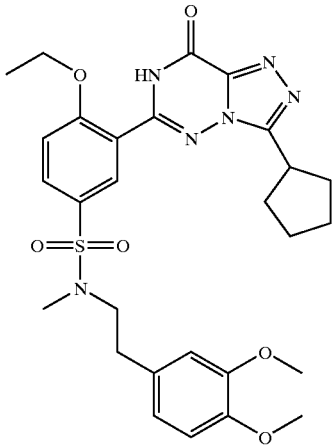

546 mg (2.8 mmol) of N-methylhomoveratrylamine and a small spatula tip of 4-DMAP are added to a suspension consisting of 395 mg (0.93 mmol) of the sulfonyl chloride from example VI in 3 ml of dichloromethane. The resulting clear solution is stirred at room temperature before it is diluted, after 7 h, with dichloromethane, washed with 1 N hydrochloric acid solution (twice) and also saturated sodium chloride, dried over magnesium chloride and concentrated in vacuo. The residue is crystallized from a little dichloromethane/ether.

Yield: 299 mg (55.1% of theory)

MS (DCI, $NH_3$): m/z (%)=583 (M+H) (100)

$^1$H-NMR (200 MHz, $CDCl_3$): δ=1.63 (t, 3 H); 1.68–2.23 (m, 8 H); 2.78–2.90 (m, 2 H); 2.82 (s, 3 H); 3.32 (t, 2 H); 3.63 (qui, 1 H); 3.84 (s, 6 H); 4.39 (q, 2 H); 6.68–6.80 (m, 3 H); 7.17 (d, 1 H); 7.89 (dd, 1 H); 8.49 (d, 1 H); 10.66 (bs, 1 H).

The sulfonamides which are listed in the following tables were prepared, by means of automated parallel synthesis, from the corresponding sulfonyl chloride (example VI) and the corresponding amines in accordance with one of the three following standard protocols.

The purity of the end products was determined by means of HPLC while they were characterized by means of LC-MS measurement. The numerical value specified in the % (HPLC) column indicates the content of the end product which is characterized by the molar peak. Standard protocol A was used in the case of amines possessing acid functionaries, standard protocol B in the case of amines possessing neutral functionalities, and standard protocol C in the case of amines possessing additional basic functionalities.

In the case of compounds which are listed in the following tables and which optically exhibit a free nitrogen valency, this latter is to be understood, in principle, as being an —NH radical.

Standard protocol A: Conversion of Amines Possessing Acid Functionalities 0.05 mmol of amine, 0.042 mmol of sulfonyl chloride and 0.10 mmol of $Na_2CO_3$ are introduced initially, and 0.5 ml of a mixture consisting of $THF/H_2O$ is pipetted in by hand. After 24 h at RT, 0.5 ml of a 1 M $H_2SO_4$ solution is added and the mixture is filtered through a two-phase cartridge (500 mg of Extrelut (upper phase) and 500 mg of $SiO_2$, mobile phase ethyl acetate). The product is obtained after concentrating the filtrate in vacuo.

Standard protocol B: Conversion of Amines Possessing Neutral Functionalities 0.125 mmol of amine is introduced initially and 0.03 mmol of sulfonyl chloride, as a solution in 1,2- dichloroethane, is pipetted in by the synthesizer. After 24 h, 0.5 ml of 1 M $H_2SO_4$ is added to the mixture and the latter is filtered through a two-phase cartridge (500 mg of Extrelut (upper phase) and 500 mg of $SiO_2$, mobile phase: ethyl acetate). The filtrate is concentrated in vacuo.

Standard protocol C: Conversion of Amines Possessing Basic Functionalities 0.05 mmol of amine is introduced initially and 0.038 mmol of sulfonyl chloride, as a solution in 1,2-dichloroethane, and 0.05 mmol of triethylamine, as absolution in 1,2-dichloroethane, are pipetted in by the synthesizer. After 24 h, 3 ml of saturated $NaHCO_3$ solution are added initially and the reaction mixture is then filtered through a two-phase cartridge. The product is obtained after the filtrate has been concentrated in vacuo.

All the reactions are monitorued by thin layer chromatography. If the reaction has not been completed after 24 hours at RT, the mixture is then heated at 60° C. for a further 12 hours and the experiment is subsequently terminated.

| Ex. No. | Structure | MW [g/mol] | HPLC-Area % at 210 nm | Mz + H |
|---------|-----------|------------|----------------------|--------|
| 3 | 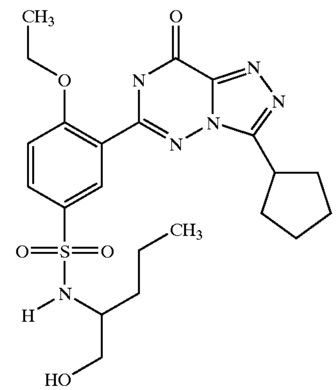 | 490.5856 | 80 | 491 |
| 4 | 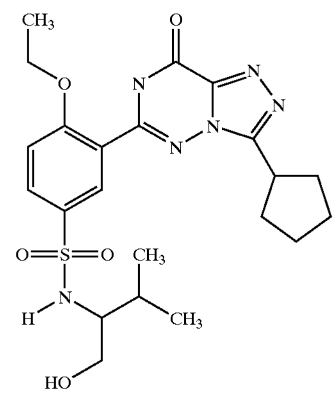 | 490.5856 | 94 | 491 |
| 5 | 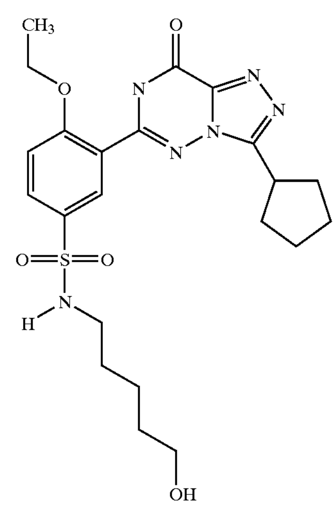 | 490.5856 | 97 | 491 |

-continued

| Ex. No. | Structure | MW [g/mol] | HPLC- Area % at 210 nm | Mz + H |
|---|---|---|---|---|
| 6 | 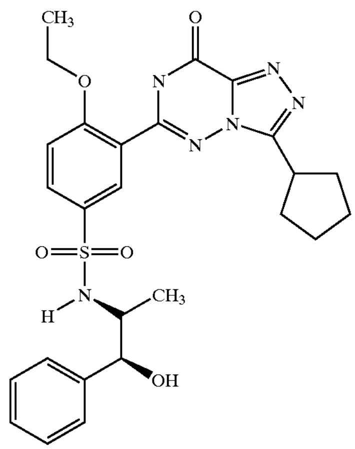 | 538.6302 | 78 | 539 |
| 7 | 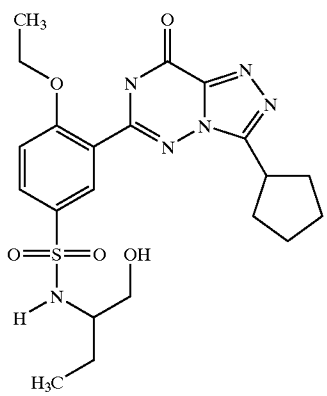 | 476.55851 | 95 | 477 |
| 8 | 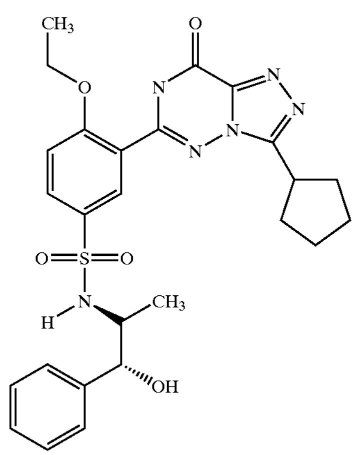 | 538.6302 | 81 | 539 |

-continued

| Ex. No. | Structure | MW [g/mol] | HPLC-Area % at 210 nm | Mz + H |
|---|---|---|---|---|
| 9 | 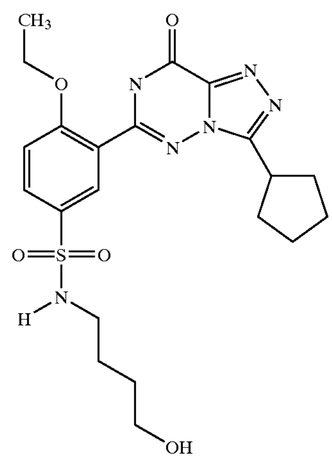 | 476.56 | 88 | 477 |
| 10 | 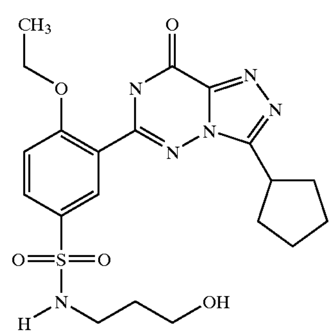 | 462.53142 | 91 | 463 |
| 11 | 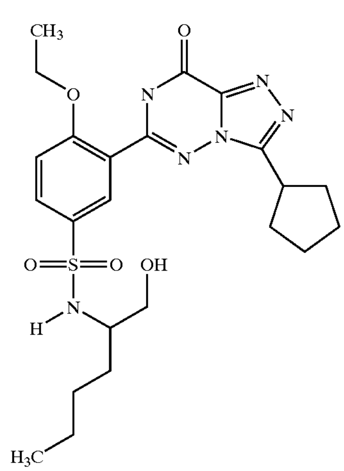 | 504.61269 | 85 | 505 |

-continued

| Ex. No. | Structure | MW [g/mol] | HPLC-Area % at 210 nm | Mz + H |
|---|---|---|---|---|
| 12 | 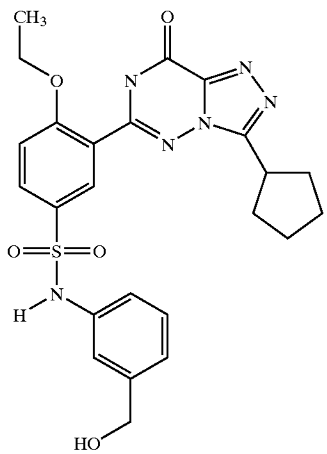 | 510.57602 | 87 | 511 |
| 13 | 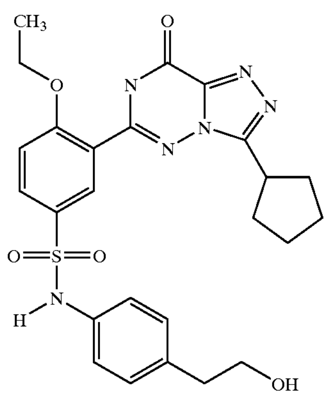 | 524.60 | 82 | 525 |
| 14 | 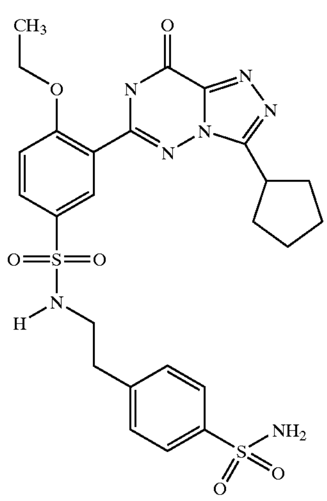 | 587.68 | 80 | 588 |

-continued

| Ex. No. | Structure | MW [g/mol] | HPLC-Area % at 210 nm | Mz + H |
|---|---|---|---|---|
| 15 | 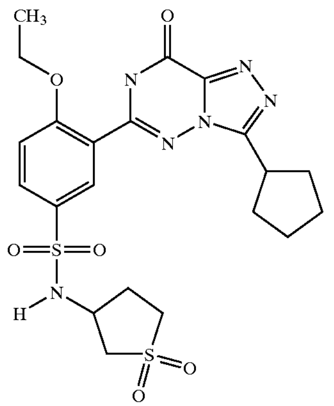 | 522.61 | 97 | 523 |
| 16 | 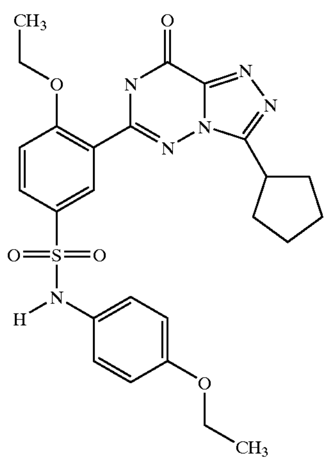 | 524.60 | 78 | 525 |
| 17 | 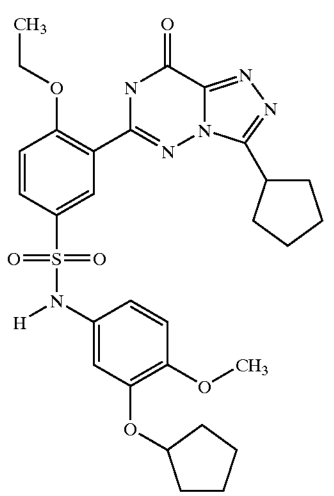 | 594.69 | 77 | 595 |

-continued
| Ex. No. | Structure | MW [g/mol] | HPLC-Area % at 210 nm | Mz + H |
|---|---|---|---|---|
| 18 | 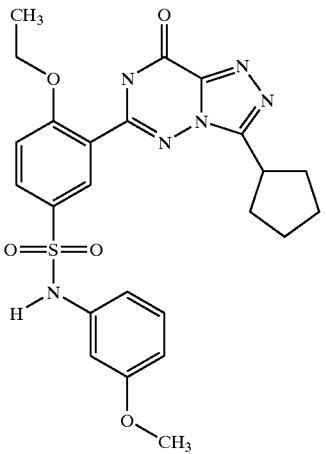 | 510.58 | 92 | 511 |
| 19 | 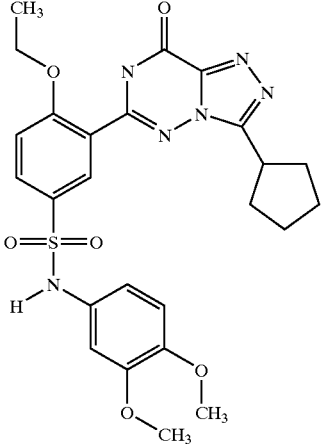 | 540.60 | 92 | 541 |
| 20 | 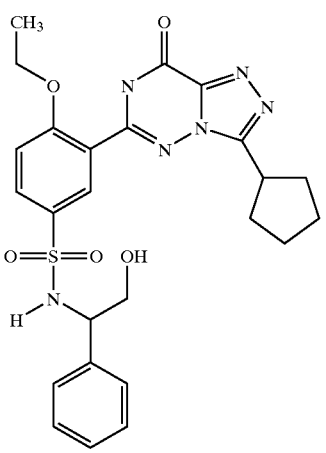 | 524.60 | 82 | 525 |

-continued

| Ex. No. | Structure | MW [g/mol] | HPLC-Area % at 210 nm | Mz + H |
|---|---|---|---|---|
| 21 | (structure) | 510.58 | 85 | 511 |
| 22 | (structure) | 528.57 | 95 | 529 |
| 23 | (structure) | 570.63 | 89 | 571 |

| Ex. No. | Structure | MW [g/mol] | HPLC-Area % at 210 nm | Mz + H |
|---|---|---|---|---|
| 24 | 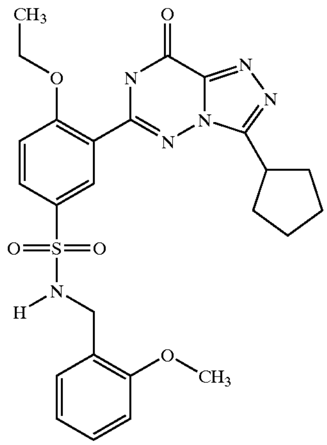 | 524.60 | 82 | 525 |
| 25 | 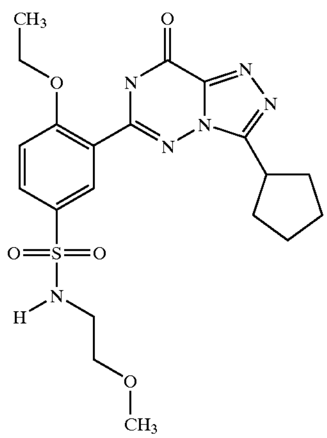 | 462.53 | 98 | 463 |
| 26 | 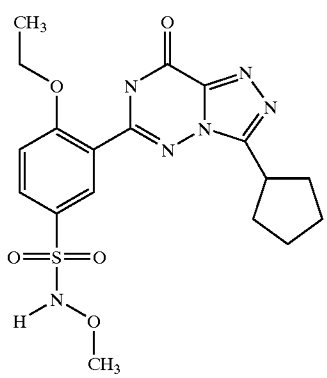 | 434.48 | 82 | 435 |

-continued

| Ex. No. | Structure | MW [g/mol] | HPLC-Area % at 210 nm | Mz + H |
|---|---|---|---|---|
| 27 | 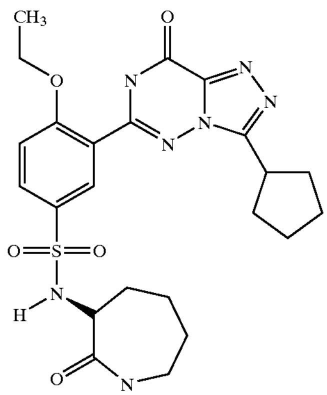 | 515.60 | 86 | 516 |
| 28 | 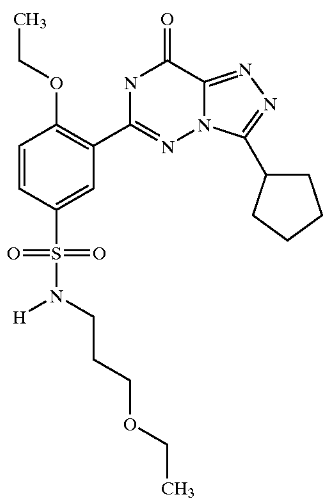 | 490.59 | 96 | 491 |
| 29 | 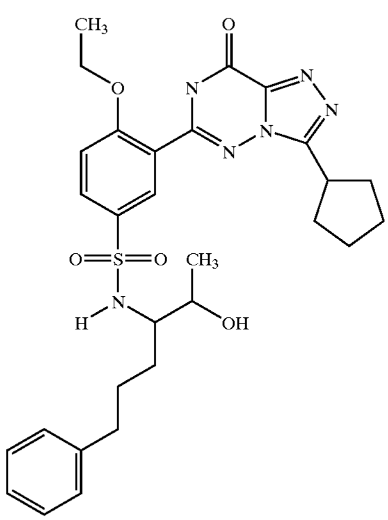 | 580.71 | 74 | 581 |

-continued
| Ex. No. | Structure | MW [g/mol] | HPLC-Area % at 210 nm | Mz + H |
|---|---|---|---|---|
| 30 | 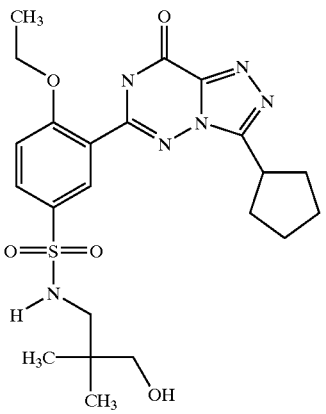 | 490.59 | 97 | 491 |
| 31 | 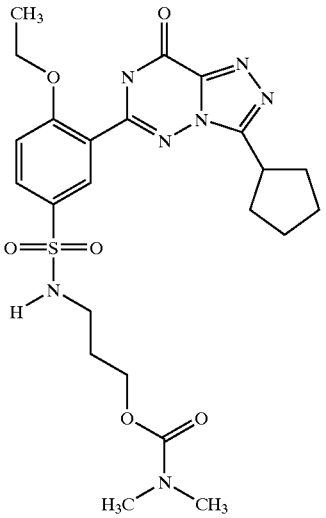 | 533.61 | 88 | 534 |
| 32 | 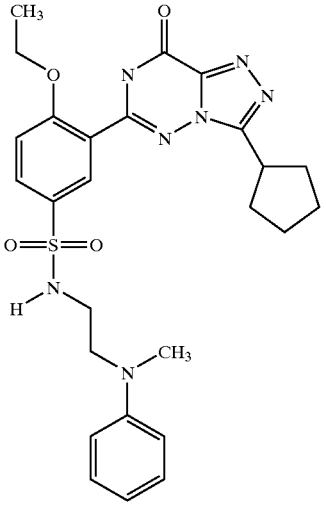 | 537.65 | 86 | 538 |

-continued
| Ex. No. | Structure | MW [g/mol] | HPLC-Area % at 210 nm | Mz + H |
|---|---|---|---|---|
| 33 | 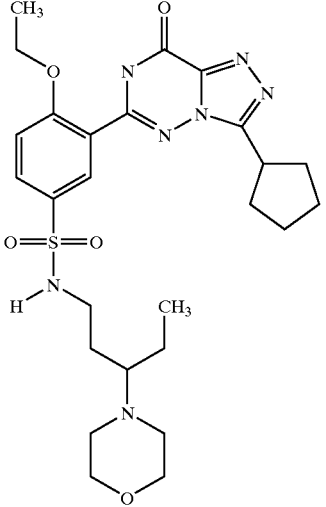 | 559.69 | 75 | 560 |
| 34 | 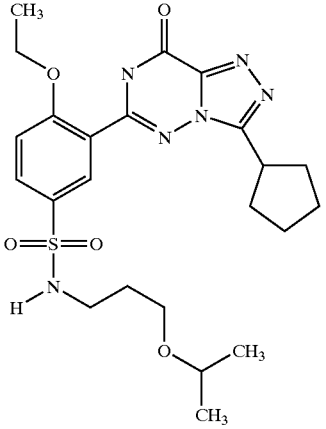 | 504.61 | 99 | 505 |
| 35 | 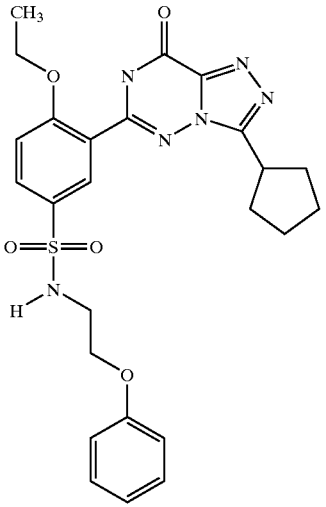 | 524.60 | 85 | 525 |

-continued
| Ex. No. | Structure | MW [g/mol] | HPLC-Area % at 210 nm | Mz + H |
|---|---|---|---|---|
| 36 | 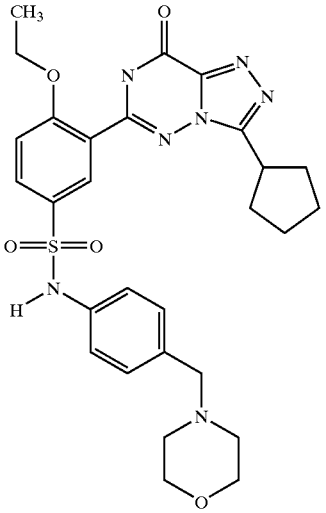 | 579.68 | 70 | 580 |
| 37 | 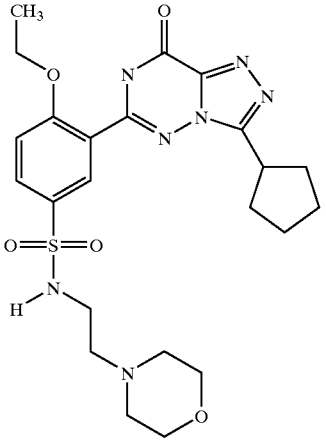 | 517.61 | 72 | 518 |
| 38 | 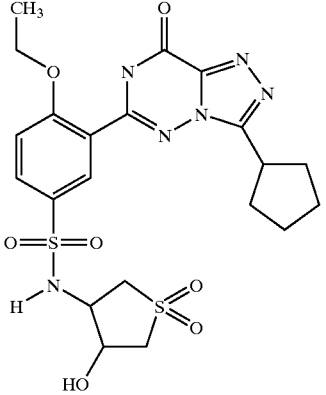 | 538.61 | 67 | 539 |

-continued
| Ex. No. | Structure | MW [g/mol] | HPLC-Area % at 210 nm | Mz + H |
|---|---|---|---|---|
| 39 | 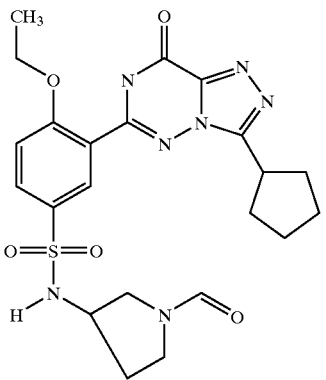 | 501.57 | 50 | 502 |
| 40 | 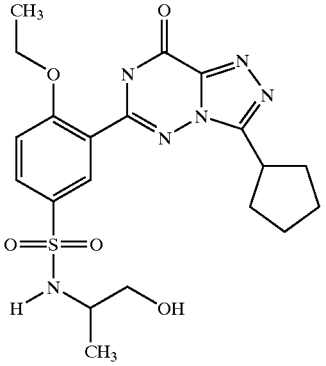 | 462.53 | 97 | 463 |
| 41 | 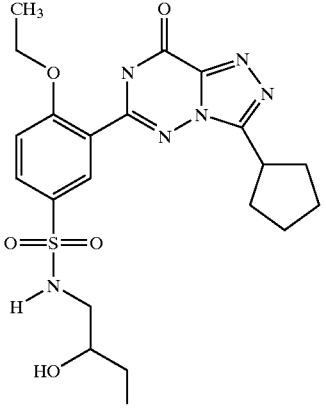 | 478.53 | 74 | 479 |

-continued

| Ex. No. | Structure | MW [g/mol] | HPLC-Area % at 210 nm | Mz + H |
|---|---|---|---|---|
| 42 | 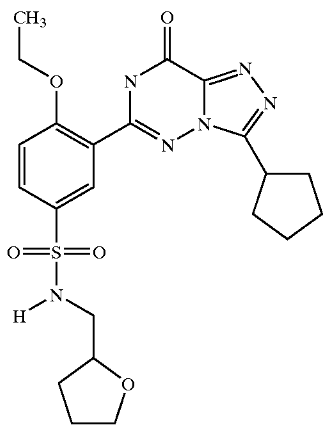 | 488.57 | 96 | 489 |
| 43 | 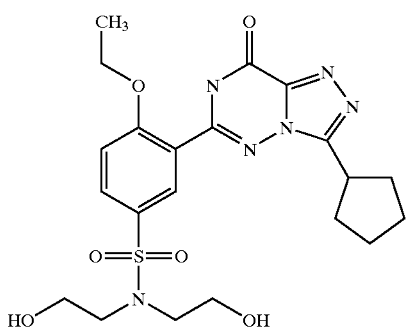 | 492.56 | 60 | 493 |
| 44 | 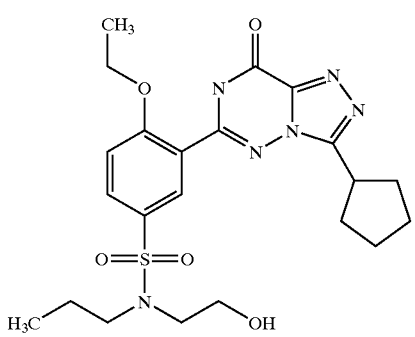 | 490.59 | 40 | 491 |
| 45 | 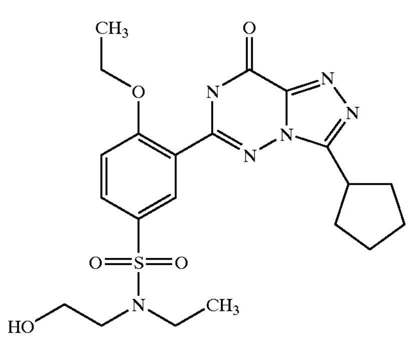 | 476.56 | 60 | 477 |

-continued

| Ex. No. | Structure | MW [g/mol] | HPLC-Area % at 210 nm | Mz + H |
|---|---|---|---|---|
| 46 | 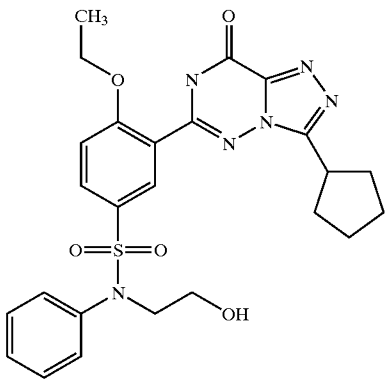 | 524.60 | 83 | 525 |
| 47 | 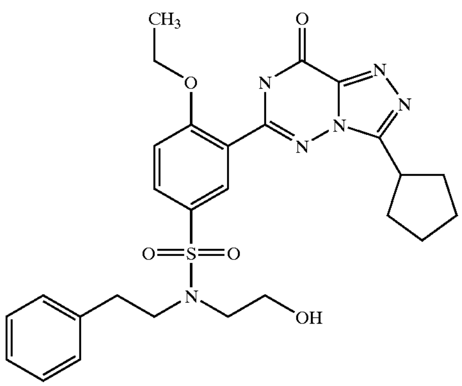 | 552.66 | 70 | 553 |
| 48 | 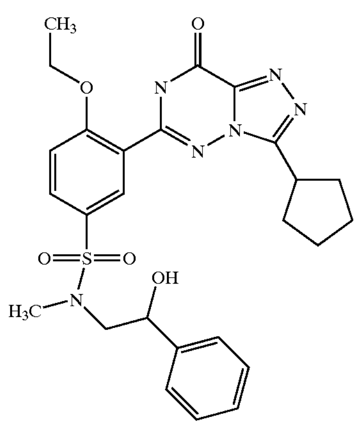 | 538.63 | 69 | 539 |
| 49 | 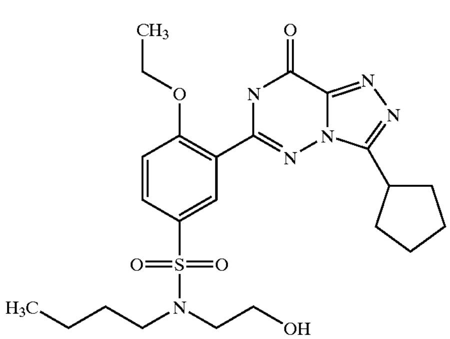 | 504.61 | 75 | 505 |

-continued
| Ex. No. | Structure | MW [g/mol] | HPLC-Area % at 210 nm | Mz + H |
|---|---|---|---|---|
| 50 | 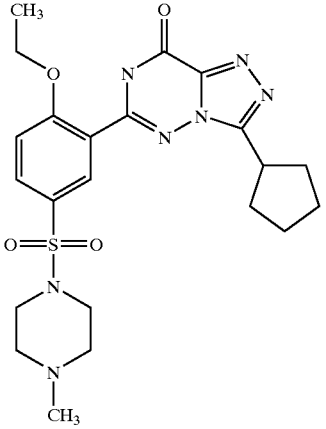 | 487.58 | 83 | 488 |
| 51 | 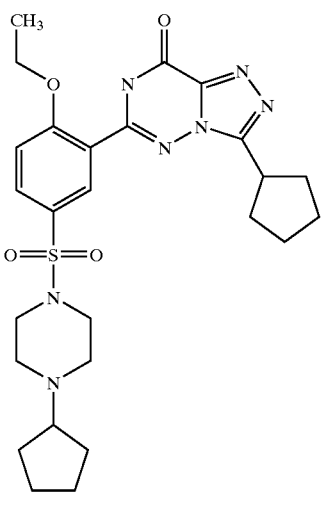 | 541.68 | 84 | 542 |
| 52 | 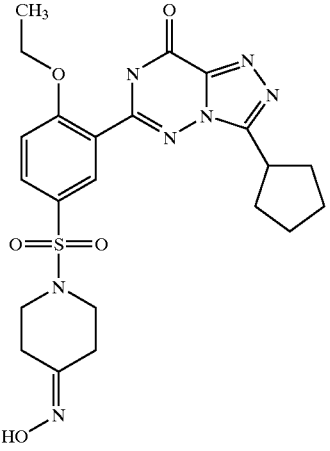 | 501.57 | 79 | 502 |

-continued

| Ex. No. | Structure | MW [g/mol] | HPLC-Area % at 210 nm | Mz + H |
|---|---|---|---|---|
| 53 | 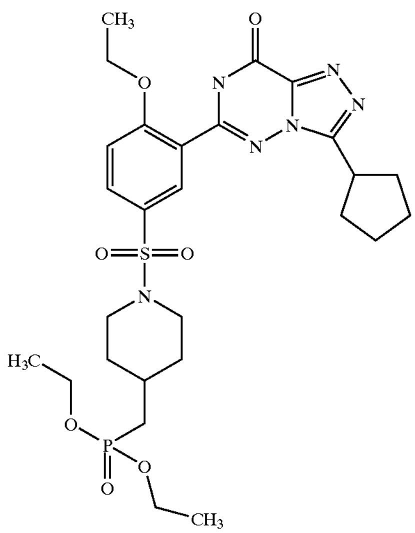 | 622.69 | 80 | 623 |
| 54 | 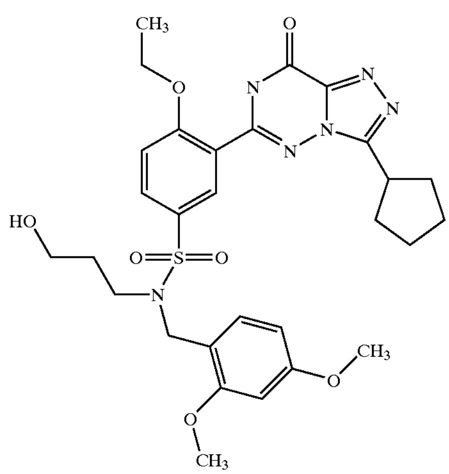 | 612.71 | 70 | 613 |
| 55 | 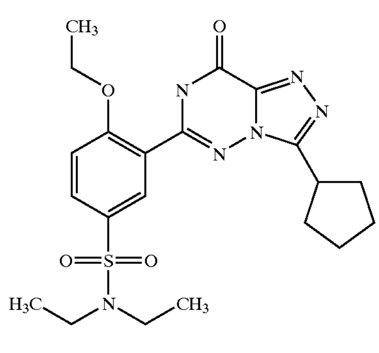 | 460.56 | 40 | 461 |

-continued

| Ex. No. | Structure | MW [g/mol] | HPLC-Area % at 210 nm | Mz + H |
|---|---|---|---|---|
| 56 | 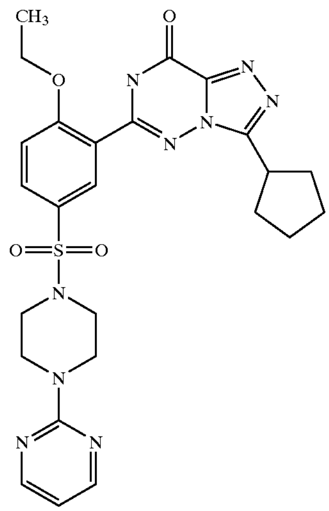 | 551.63 | 75 | 552 |
| 57 | 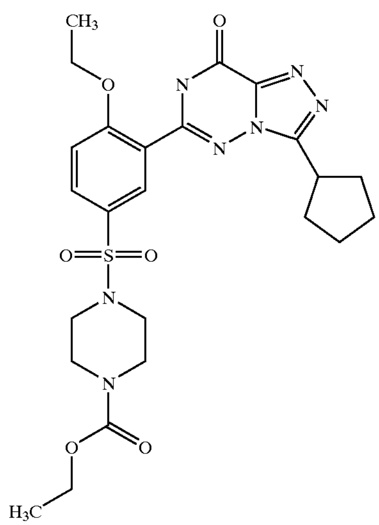 | 545.62 | 79 | 546 |
| 58 | 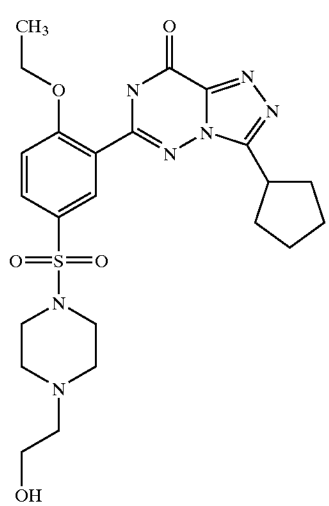 | 517.61 | 55 | 518 |

-continued

| Ex. No. | Structure | MW [g/mol] | HPLC-Area % at 210 nm | Mz + H |
|---|---|---|---|---|
| 59 | 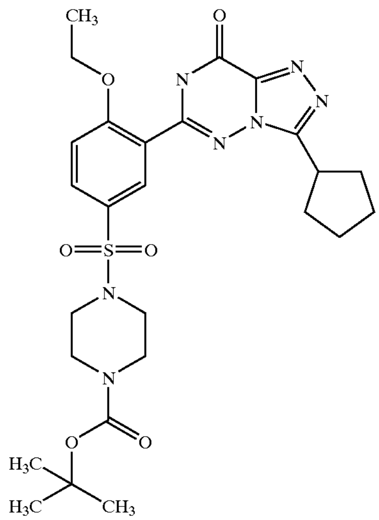 | 573.68 | 75 | 574 |
| 60 | 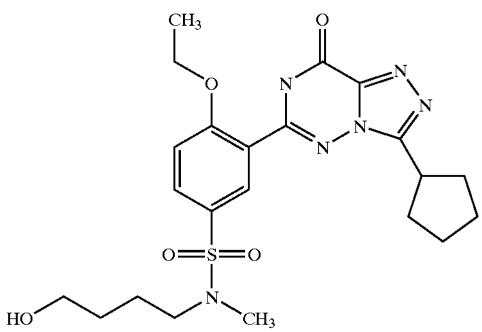 | 490.59 | 61 | 491 |
| 61 | 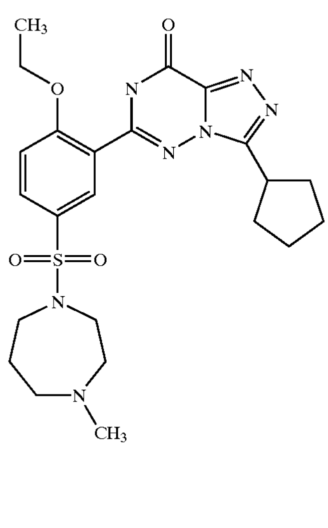 | 501.61 | 86 | 502 |

-continued

| Ex. No. | Structure | MW [g/mol] | HPLC-Area % at 210 nm | Mz + H |
|---|---|---|---|---|
| 62 | 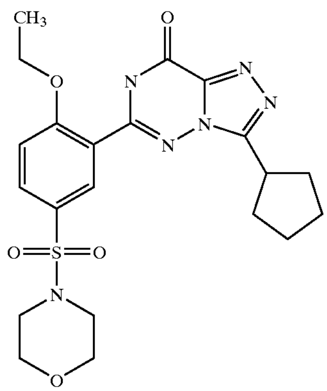 | 474.54 | 75 | 475 |
| 63 | 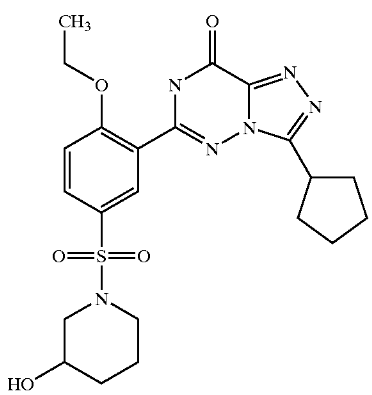 | 488.57 | 77 | 489 |
| 64 | 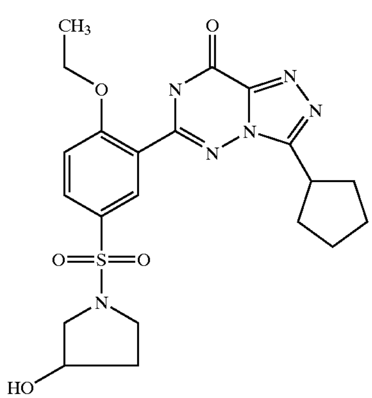 | 474.54 | 70 | 475 |

-continued

| Ex. No. | Structure | MW [g/mol] | HPLC-Area % at 210 nm | Mz + H |
|---|---|---|---|---|
| 65 | 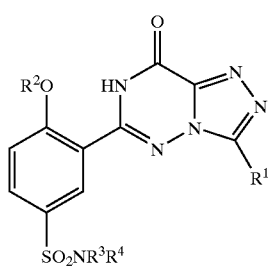 | 501.61 | 64 | 502 |

What is claimed is:

1. A triazolotriazinone of the formula (I)

(I),

[structure of formula I]

in which

R$^1$ represents straight-chain or branched alkyl having up to 6 carbon atoms or represents (C$_3$–C$_8$)-cycloalkyl, R$^2$ represents hydrogen or represents straight-chain or branched alkyl having up to 6 carbon atoms, R$^3$ and R$^4$ are identical or different and represent hydrogen or (C$_1$–C$_6$)-alkoxy or represent (C$_1$–C$_6$)-alkyl which is optionally substituted, up to 3 times, identically or differently, by hydroxyl, (C$_1$–C$_5$)-alkoxy or phenoxy or by radicals of the formulae —O—CO—NR$^5$R$^6$, —NR$^7$R$^8$ or

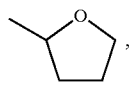, in which

R$^5$, R$^6$, R$^7$ and R$^8$ are identical or different and denote hydrogen, (C$_1$–C$_6$)-alkyl or phenyl, or R$^7$ and R$^8$, together with the nitrogen atom to which they are bonded, form a 5- to 6-membered, saturated heterocycle which can additionally contain a further heteroatom from the series S and O, and/or (C$_1$–C$_6$)-alkyl is, for its part, optionally substituted by phenyl which is optionally substituted, up to 3 times, identically or differently, by hydroxyl, (C$_1$–C$_6$)-alkoxy or halogen or by (C$_1$–C$_6$)-alkyl which, for its part, is in turn substituted by hydroxyl or (C$_1$–C$_6$)-alkoxy, or phenyl is optionally substituted by radicals of the formulae —SO$_2$—NR$^9$R$^{10}$ or —NR$^{11}$R$^{12}$, in which R$^9$, R$^{10}$, R$^{11}$ and R$^{12}$ are identical or different and denote hydrogen, (C$_1$–C$_6$)-alkyl or phenyl, or R$^{11}$ and R$^{12}$, together with the nitrogen atom to which they are bonded, form a 5- to 6-membered, saturated heterocycle which can additionally contain a further beteroatom from the series S and O, or R$^3$ represents hydrogen or (C$_1$–C$_6$)-alkyl, and R$^4$ represents radicals of the formula

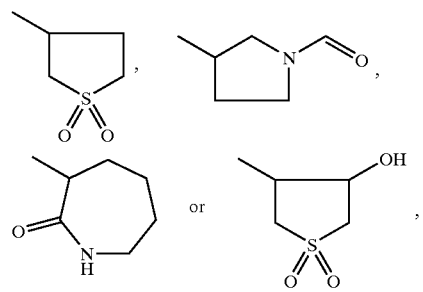

or represents phenyl which is optionally substituted, up to 3 times, identically or differently, by halogen, (C$_1$–C$_6$)-alkoxy or hydroxyl or by a radical of the formula

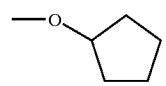

or by (C$_1$–C$_6$)-alkyl which, for its part, can be substituted by hydroxyl or (C$_1$–C$_6$)-alkoxy, or R$^3$ and R$^4$, together with the nitrogen atom to which they are bonded, form a radical of the formula

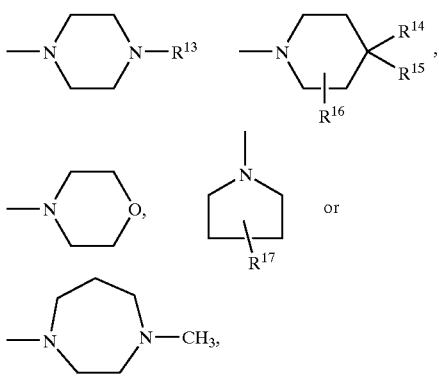

in which
R$^{13}$ denotes hydrogen, (C$_1$–C$_6$)-alkoxycarbonyl, (C$_3$–C$_6$)-cycloalkyl, pyridyl, pyrimidyl or (C$_1$–C$_6$)-alkyl which is optionally substituted by hydroxyl,
R$^{14}$ and R$^{15}$ are identical or different and denote hydrogen, hydroxyl or (C$_1$–C$_6$)-alkyl which is optionally substituted by hydroxyl or by a radical of the formula —P(O)(OR$^{18}$)(OR$^{19}$), in which
R$^{18}$ and R$^{19}$ are identical or different and denote hydrogen or (C$_1$–C$_6$)-alkyl, or
R$^{14}$ and R$^{15}$ together form a radical of the formula =N—OH,
R$^{16}$ and R$^{17}$ are identical or different and denote hydrogen or (C$_1$–C$_6$)-alkyl which is optionally substituted by hydroxyl, and the salts, N-oxides and isomeric forms thereof.

2. A triazolotriazinone of the formula (I) as claimed in claim 1, in which
R$^1$ represents straight-chain or branched alkyl having up to 5 carbon atoms, or represents cyclopropyl, cyclopentyl or cyclohexyl,
R$^2$ represents straight-chain or branched alkyl having up to 4 carbon atoms,
R$^3$ and R$^4$ are identical or different and represent hydrogen or methoxy or represent (C$_1$–C$_5$)-alkyl which is optionally substituted, up to 3 times, identically or differently, by hydroxyl, (C$_1$–C$_4$)-alkoxy or phenoxy or by groups of the formulae —O—CO—NR$^5$R$^6$, —NR$^7$R$^8$ or

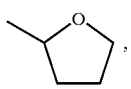

in which
R$^5$, R$^6$, R$^7$ and R$^8$ are identical or different and denote hydrogen, (C$_1$–C$_4$)-alkyl or phenyl, or
R$^7$ and R$^8$, together with the nitrogen atom to which they are bonded, form a morpholine, piperidine or pyrrolidine ring,
and/or (C$_1$–C$_5$)-alkyl is, for its part, optionally substituted by phenyl which can be optionally substituted, up to 3 times, identically or differently, by hydroxyl or (C$_1$–C$_4$)-alkoxy or by (C$_1$–C$_4$)-alkyl which, for its part, is in turn substituted by hydroxyl or (C$_1$–C$_4$)-alkoxy, or phenyl is optionally substituted by radicals of the formulae —SO$_2$—NR$^9$R$^{10}$ or —NR$^{11}$R$^{12}$, in which
R$^9$, R$^{10}$, R$^{11}$ and R$^{12}$ are identical or different and denote hydrogen, (C$_1$–C$_4$)-alkyl or phenyl, or R$^{11}$ and R$^{12}$, together with the nitrogen atom to which they are bonded, form a morpholine, piperidine or pyrrolidine ring, or R$^3$ represents hydrogen or (C$_1$–C$_4$)-alkyl, and R$^4$ represents radicals of the formula

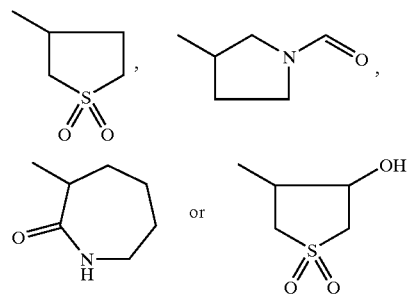

or represents phenyl which is optionally substituted, up to 3 times, identically or differently, by fluorine, (C$_1$–C$_4$)-alkoxy or hydroxyl, by a radical of the formula

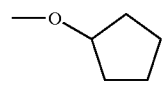

or by (C$_1$–C$_4$)-alkyl which can, for its part, be substituted by hydroxyl or (C$_1$–C$_3$)-alkoxy, or R$^3$ and R$^4$, together with the nitrogen atom to which they are bonded, form a radical of the formula

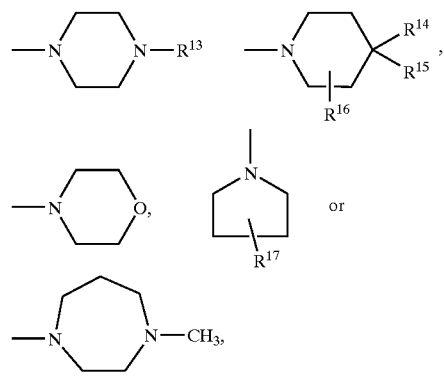

in which
R$^{13}$ denotes hydrogen, (C$_1$–C$_4$)-alkoxycarbonyl, cyclopentyl, cyclohexyl, pyridyl, pyrimidyl or (C$_1$–C$_5$)-alkyl which is optionally substituted by hydroxyl,
R$^{14}$ and R$^{15}$ are identical or different and denote hydrogen or (C$_1$–C$_5$)-alkyl which is optionally substituted by hydroxyl or by a radical of the formula —P(O)(OR$^{18}$)(OR$^{19}$), in which
R$^{18}$ and R$^{19}$ are identical or different and denote hydrogen, methyl or ethyl, or
R$^{14}$ and R$^{15}$ together form a radical of the formula =N—OH, $R^{16}$ and $R^{17}$ are identical or different and denote hydrogen, hydroxyl or $(C_1-C_3)$-alkyl which is optionally substituted by hydroxyl, and the salts, N-oxides and isomeric forms thereof.

3. A triazolotriazinone of the formula (I) as claimed in claim 1, in which $R^1$ represents straight-chain or branched alkyl having up to 3 carbon atoms or represents cyclopentyl, $R^2$ represents straight-chain or branched alkyl having up to 3 carbon atoms, $R^3$ and $R^4$ are identical or different and represent hydrogen or methoxy or represent $(C_1-C_4)$-alkyl which is optionally substituted, up to 3 times, identically or differently, by hydroxyl, $(C_1-C_4)$-alkoxy or phenoxy or by groups of the formulae —O—CO—$NR^5R^6$, —$NR^7R^8$ or in which $R^5$, $R^6$, $R^7$ and $R^8$ are identical or different and denote hydrogen, $(C_1-C_3)$-alkyl or phenyl, or $R^7$ and $R^8$, together with the nitrogen atom to which they are bonded, form a morpholine, piperidine or pyrrolidine ring, and/or $(C_1-C_4)$-alkyl is, for its part, optionally substituted by phenyl which is optionally substituted, up to 3 times, identically or differently, by hydroxyl, $(C_1-C_3)$-alkoxy or fluorine or by $(C_1-C_3)$-alkyl which is for its part in turn substituted by hydroxyl or $(C_1-C_4)$-alkoxy, or phenyl is optionally substituted by radicals of the formulae —$SO_2$—$NR^9R^{10}$ or —$NR^{11}R^{12}$, in which $R^9$, $R^{10}$, $R^{11}$ and $R^{12}$ are identical or different and denote hydrogen, $(C_1-C_3)$-alkyl or phenyl, or $R^{11}$ and $R^{12}$, together with the nitrogen atom to which they are bonded, form a morpholine, piperidine or pyrrolidine ring, or $R^3$ represents hydrogen or methyl, and $R^4$ represents radicals of the formula or represents phenyl which is optionally substituted, up to 3 times, identically or differently, by fluorine, methoxy or hydroxyl, by a radical of the formula or by $(C_1-C_4)$-alkyl which, for its past, can be substituted by hydroxyl or methoxy or ethoxy, or $R^3$ and $R^4$, together with the nitrogen atom to which they are bonded, form a radical of the formula in which $R^{13}$ denotes hydrogen, $(C_1-C_4)$-alkoxycarbonyl, cyclopentyl, pyrimidyl or $(C_1-C_3)$-alkyl which is optionally substituted by hydroxyl, $R^{14}$ and $R^{15}$ are identical or different and denote $(C_1-C_3)$-alkyl which is optionally substituted by hydroxyl or by a radical of the formula —P(O)(OR$^{18}$)(OR$^{19}$), in which $R^{18}$ and $R^{19}$ denote ethyl, or $R^{14}$ and $R^{15}$ together form a radical of the formula =N—OH, $R^{16}$ and $R^{17}$ are identical or different and denote hydrogen or $(C_1-C_3)$-alkyl which is optionally substituted by hydroxyl, and the salts, N-oxides and isomeric forms thereof.

4. A triazolotriazinone of the formula (I) as claimed in claim 1 and possessing one of the following structures:

Structure

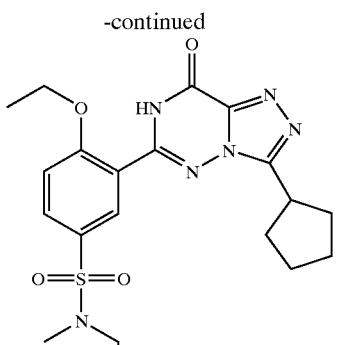
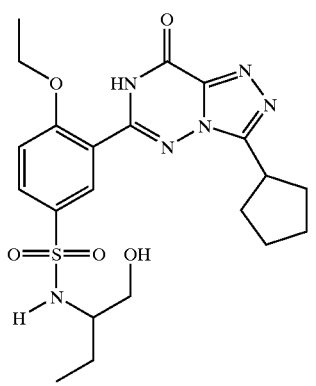
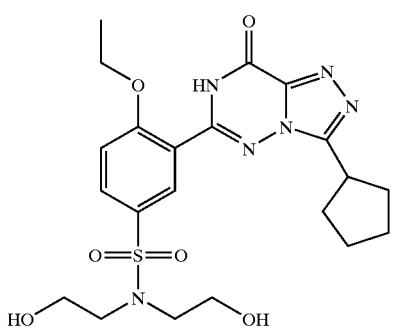
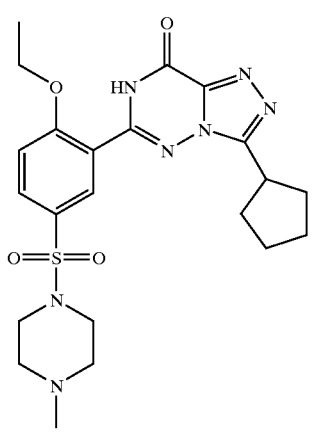
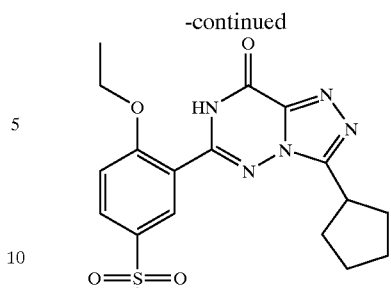
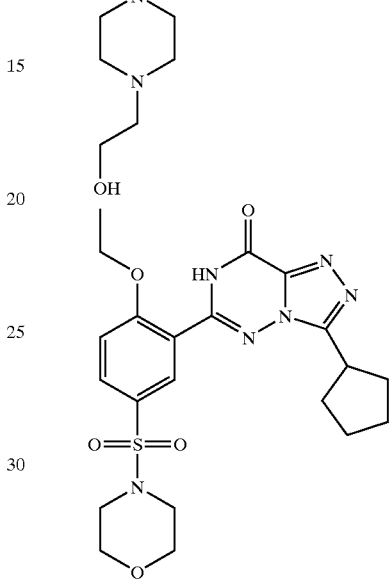
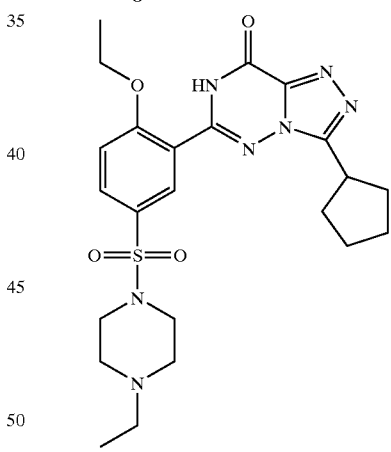
5. A process for preparing triazolotriazinones as claimed in claim 1, characterized in that compounds of the formula (II)
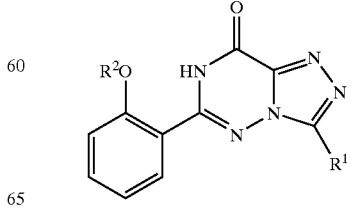

in which
R¹ and R² have the meaning indicated in claim 1, are reacted with chlorosulfonic acid (ClSO₃H), where appropriate in inert solvents and where appropriate in the presence of a base, to give the compounds of the formula (III)

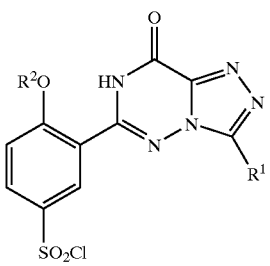
(III), in which
R¹ and R² have the meaning indicated in claim 1, and subsequently reacted with amines of the formula (IV)

$$HNR^3R^4 \qquad (IV),$$

in which
R³ and R⁴ have the meaning indicated in claim 1.

6. A pharmaceutical composition which comprises one or more compounds of formula (I) as claimed in one of claims 1 to 4 and also one or more pharmacologically harmless auxiliary substances and carrier substances.

7. A method for the treatment of diseases of the urogenital system selected from the group consisting of prostate hypertrophy, incontinence, erectile dysfunction and female sexual dysfunction comprising administering to a subject in need of such treatment an effective amount of a compound of the formula (I) as claimed in one of claims 1 to 4.

* * * * *